United States Patent [19]

van der Mass

[11] 4,450,295
[45] May 22, 1984

[54] METHOD OF MANUFACTURING ANHYDROUS 2-HYDROXY-3-CHLOROPROPANE TRIMETHYLAMMONIUM CHLORIDE

[75] Inventor: Hendrikus J. H. van der Mass, Zuilichem, Netherlands

[73] Assignee: Chemische Fabriek Zaltbommel, B.V., Zaltbommel, Netherlands

[21] Appl. No.: 332,117

[22] Filed: Dec. 18, 1981

[30] Foreign Application Priority Data

Dec. 31, 1980 [NL] Netherlands .................. 8007126

[51] Int. Cl.³ ............................................. C07C 89/00
[52] U.S. Cl. .................................... 564/294; 564/292
[58] Field of Search ................ 564/292, 293, 497, 294

[56] References Cited

U.S. PATENT DOCUMENTS

| | | | |
|---|---|---|---|
| 2,876,217 | 3/1959 | Paschall | 536/50 |
| 4,032,411 | 6/1977 | Tornquist et al. | 203/14 |
| 4,269,665 | 5/1981 | Barnes et al. | 203/14 |

FOREIGN PATENT DOCUMENTS 5223 11/1979 European Pat. Off. ............ 504/292

OTHER PUBLICATIONS

Perry, "Chem. Eng. Handbook", pp. 13/46 to 13/51, (1963), McGraw–Hill.

*Primary Examiner*—James H. Reamer
*Attorney, Agent, or Firm*—Felfe & Lynch

[57] ABSTRACT

Process for manufacturing anhydrous 2-hydroxy-3-chlorophropane trialkylammonium chloride by conversion of trialkylammonium chloride with epichlorohydrin by forming an aqueous solution of trialkylammonium chloride in an organic solvent inert to epichlorohydrin, the solvent forming an azeotrope with ater which boils at temperatures up to the normal boiling point of the solvent, distilling off the azeotrope to form a suspension of trialkylammonium chloride in the solvent reaction product and reacting the reaction product in the solvent with epichlorohydrin at a temperature of 20° to 120° C.

5 Claims, No Drawings

METHOD OF MANUFACTURING ANHYDROUS 2-HYDROXY-3-CHLOROPROPANE TRIMETHYLAMMONIUM CHLORIDE

The invention relates to a method of manufacturing 2-hydroxy-3-chloropropane trimethylammonium chloride by converting trialkylammonium chloride with epichlorohydrin.

Converting trimethylammonium chloride with epichlorohydrin to form 2-hydroxy-3-chloropropane trimethylammonium chloride is known, from U.S. Pat. No. 2,876,217 for example. In the known process the trimethylammonium chloride is employed in an aqueous solution and the reaction product is an aqueous solution of 2-hydroxy-3-chloropropane trimethylammonium chloride. This aqueous solution must usually be purified before it can be used to manufacture cation-active starch products.

A disadvantage of the method described in U.S. Pat. No. 2,876,217 is the necessity of working with an aqueous medium, which leads to a series of side reactions like the formation of 1,3-bis-trimethylammonium-2-hydroxypropane dichloride. This byproduct precipitates with and usually can not be separated from the desired product, of which it is an undesirable component because it does not react with starch.

1,3-Dichloropropanol-2 will also occur with the method disclosed in U.S. Pat. No. 2,876,217 because of the reaction of the epichlorohydrin with hydrochloric acid. Since this propanol reacts with starch during cross-linkage, its participation in the final product must be limited to less than 50 ppm.

Obtaining an anhydrous 2-hydroxy-3-chloropropane trimethylammonium chloride as the precipitate from an anhydrous organic solvent and filtering out the crystals has been proposed (Cf. NR-OS 78 04 880). This method starts with gaseous trimethylamine, which reacts with the solvent. Since, however, the solvent is dangerous to health, it is difficult to carry out this process on an industrial scale without detrimentally affecting the atmosphere in the work place.

The problem remains, then, of how to manufacture an anhydrous form of 2-hydroxy-3-chloropropane trialkylammonium chloride from an aqueous initial solution of trialkylammonium chloride, obtaining a high yield of a product that is as pure as possible and that contains as little of such byproducts as 1,3-bis-trimethylammonium-2-hydroxypropane chloride or 1,3-dichloropropanol-2.

As a solution to this problem a method has been discovered for manufacturing anhydrous 2-hydroxy-3-chloropropane trialkylammonium dichloride by converting trialkylammonium chloride with epichlorohydrin, characterized by making an aqueous solution of trialkylammonium chloride in an organic solvent that combines with water to form an azeotrope boiling at temperatures below its normal boiling point, by heating the solution to temperatures as high as the boiling point of the solvent, by distilling the azeotrope off as it forms, and finally by converting in the solvent with epichlorohydrin at temperatures ranging from 20° to 120° C.

This method leads directly to yields of over 80% of the desired product in solid form. The product is up to 99.8% pure as determined by its chlorohydrin content and by nuclear magnetic resonance. It is thus practically free of 1,3-bis-trialkylammonium-2-hydroxypropane chloride when manufactured in accordance with the preferred embodiment of the method.

It is important to select the right solvent when employing this method. The solvent must form an azeotrope with water, and the boiling point of the azeotrope must be below that of the solvent alone. The azeotrope should also be easy to separate into layers. The solvent or mixture of solvents must also not react with epichlorohydrin under the prevailing reaction conditions. This prerequisite is generally satisfied by organic solvents that do not readily form a solution with water. Among such solvents are aliphatic alcohols with 4 to 6 carbon atoms, aliphatic saturated hydrocarbons with 5 to 8 carbon atoms, aromatic hydrocarbons like toluene and benzene, trichloroethylene, tetrachloroethylene, and methyl ethyl ketone. Mixtures of these substances may also be employed. Since the mixtures often work better than the individual solvents, one preferred embodiment of the method employs mixtures.

Among preferred mixtures are combinations of aliphatic alcohols with toluene or benzene in proportions that will result in an azeotropic mixture. Mixtures of other applicable solvents must also be azeotropic.

In the first stage of the method of the invention a hydrous solution of trialkylammonium chloride is dissolved in or dispersed through the solvent or mixture of solvents. A 60 to 75% aqueous solution is usually employed, although higher or lower concentrations can also be used. It is practical to use a solution of trialkylammonium chloride that will not have to be further diluted, to avoid having to distill too much water out later.

The amount of trialkylammonium chloride solution to be employed depends on how readily the solvent selected will dissolve the salt. About 5 to 8 mol of trialkylamine hydrochloride per 2000 g of solvent or solvents is usually employed. Lower concentrations of trialkylamine hydrochloride may also be used, of course, although there would be no advantage to doing so.

The trialkylamine hydrochloride solution is then heated in the organic solvent or solvents to the boiling point of the solvent or solvents and the resulting azeotropic mixture reflux-distilled out. Water is separated from the azeotrope distillate by a known method (by decanting for instance) and the recovered solvent returned if possible to the reaction mixture. The materials can also be fractionated, with only the azeotropic mixture distilling over. Heating continues until an amount of water equal to that of the original aqueous solution of trialkylamine hydrochloride is left in the distillate. How long this takes can easily be determined with preliminary tests and is a function of several known factors.

As the water is being distilled off, some or all, depending on the selected reaction medium, of the trialkylammonium chloride should precipitate in solid form. This precipitation will not affect the further course of the reaction, although care must be taken that the resulting dispersion remains easy to stir. More anhydrous solvent or solvents may be added if necessary. After the azeotropic distillation of the water, any solvent, like a lower, water-miscible alcohol, can be added.

Epichlorohydrin, preferably in equimolar amounts, is added to the solution or suspension after the water has been distilled off. The reaction with trialkylammonium chloride will begin at only slightly elevated temperatures. Temperatures will range preferably from 40° to 60° C. Since conversion is exothermic, the mixture may have to be cooled. The reaction may be followed by determining the epichlorohydrin content of the solution by gas-chromatography. The desired end-product will precipitate into the solvent or solvents in the form of a white, crystalline powder. When the reaction stops, the product can be filtered out directly and processed further by known methods to obtain the grade of purity mentioned above.

The preferred trialkylammonium chloride is trimethylammonium chloride. Other possible alkyl groups are those with 2 to 4 carbon atoms. The alkyl groups may also be different.

EXAMPLE 1

A 3-l round-bottom flask equipped with a stirrer, a thermometer, a drop funnel, and a still with water separator and reflux condenser was charged with 2100 ml of toluene, to which 680 g of a 70% aqueous solution of trimethylammonium chloride was added. The theoretical trimethylammonium chloride content was 5 mol.

The mixture was heated to the boiling point and the water distilled off azeotropically and separated for 6 hours. A total of 201 ml of water was collected. A total of 462.5 g of epichlorohydrin was added to the remaining mass of crystals and toluene for 1½ hours at an initial temperature of 70° to 75° C., while the internal temperature increased to between 98° and 100° C. When all the epichlorohydrin had been added, the reaction mixture was stirred 6 hours longer while it gradually cooled.

The resulting solid was filtered out, rewashed, first with toluene and then with acetone, and dried in a vacuum. The yield was 812 g of a white powder, 83.7% in terms of trimethylamine hydrochloride.

EXAMPLE 2

The apparatus described in Example 1 was charged with 2000 ml of trichloroethylene, to which 543 g of a 70% aqueous solution of trimethylammonium chloride was added. The mixture was heated to the boiling point and an azeotropic mixture of trichloroethylene and water distilled off for 11 hours. A total of 159.5 ml of water was collected.

The resulting mixture was cooled to 75° C., at which temperature the addition of epichlorohydrin was commenced. A total of 370.1 g (4 mol) of epichlorohydrin was allowed to drip into the mixture for 3 hours, while the internal temperature of the mixture increased to 90° C. The reaction mixture was stirred 2 hours longer until gas chromatography indicated no more epichlorohydrin.

The resulting solid was filtered out, washed with trichloroethane, and dried. A total of 672 g, with an active content of 93.4% was obtained, a yield of 83.5% in terms of trimethylammonium chloride.

EXAMPLE 3

The apparatus described in Example 1 was charged with 2000 ml of methyl isobutyl ketone, to which 545.7 g of a 70% aqueous solution of trimethylammonium chloride was added. The water was distilled off as an azeotropic mixture. A total of 160.4 ml of water was collected in 7 hours.

The mixture was cooled to 80° C., and 370.7 g of epichlorohydrin added for 5 hours, while the temperature increased to between 90° and 95° C. The resulting product was immediately filtered out without further stirring, washed with methyl isobutyl ketone, and dried in a vacuum.

A total of 577 g of 2-hydroxy-3-chloropropane trimethylammonium chloride, 97 to 98% pure, was obtained. This yield was 75.1%.

EXAMPLE 4

The three-necked flask described in Example 1 was charged with 2000 ml of n-butyl alcohol, which was heated to an internal temperature of 117° C. while being reflux distilled. Into this was dripped 1090 g of a 70% aqueous solution of trimethylamine hydrochloride for 4 hours, while the internal temperature decreased to between 95° and 98° C. The mixture was kept at this temperature and reflux-distilled for 8 hours, with a total of 306 g of water and butanol collected. This mixture contained about 285 ml of water.

The reaction mixture was cooled to between 60° and 70° C. and 740 g of epichlorohydrin added for 3 hours. The temperature rose so rapidly that the mixture had to be cooled. When all the epichlorohydrin had been added, the mixture was stirred for 5 hours. The resulting solid was filtered out, washed with butanol, and immediately dried. The yield was 1373 g of 88 to 93% pure 2-hydroxy-3-chloropropane trimethylammonium chloride.

EXAMPLE 5

A 3-l three-necked flask was charged with a mixture of 540 g of n-butyl alcohol and 1460 g of toluene. This mixture boils at 105.6° C. It was reflux heated to this boiling point. Into it was dripped 1090 g of a 70% aqueous solution of trimethylamine hydrochloride, with the interior temperature decreasing to 100° C. Reflux was continued for 7 hours and the aqueous azeotropic mixture was collected, resulting in 335 g of a distillate that was 97.8% water.

The crystalline residue of trimethylammonium chloride was cooled in the toluene-alcohol mixture to 50° C. To it was added 740 g of epichlorohydrin for 3½ hours. The temperature was kept at or below 70° C. by cooling. After all the epichlorohydrin had been added, the mixture was stirred for another 4 hours until gas chromatography indicated no more epichlorohydrin.

The reaction mixture was cooled and the solid matter filtered out, rewashed with toluene, and dried. The yield was 1299 g of a white crystalline powder with an active content of from 99.6 to 99.7% of 2-hydroxy-3-chloropropane methylammonium chloride. Only 24 ppm of dichloropropanol were demonstrable.

It will be understood that the specification and examples are illustrative but not limitative of the present invention and that other embodiments within the spirit and scope of the invention will suggest themselves to those skilled in the art.

What is claimed is:

1. Process for manufacturing anhydrous 2-hydroxy-3-chloropropane trialkylammonium chloride by the conversion of trialkylammonium chloride with epichlorohydrin, which process comprises forming an aqueous solution of the trialkylammonium chloride in an organic solvent which is non-reactive towards epichlorohydrin and does not readily form a solution with water but combines with water to form an azeotrope which boils at temperatures up to the boiling point of the solvent, except for tetrachloroethane; distilling off the azeotrope as it is formed, separating off the water to form a suspension of trialkylammonium chloride in solvent reaction product; and reacting the reaction product in the solvent with epichlorohydrin at a temperature of 20° to 120° C.

2. Process as claimed in claim 1, wherein the reaction with epichlorohydrin is carried out at temperatures ranging from 40° to 60° C.

3. Process as claimed in claim 1, wherein the separate steps of the process are carried out partly or entirely in a mixture of organic solvents.

4. The process of claim 3 wherein the mixture of solvents comprises combinations of aliphatic alcohols with toluene or benzene in proportions that will result in an azeotropic mixture.

5. The process of claim 1 wherein said organic solvent is an aliphatic alcohol with 4 to 6 carbon atoms, toluene, benzene, trichloroethylene, tetrachloroethylene, as methyl ethyl ketone.

* * * * *